Figure 2:
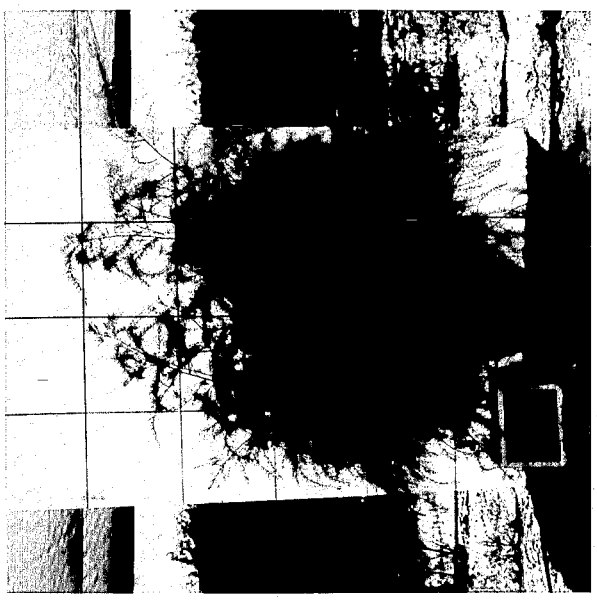

US00PP08318P

United States Patent [19]

Ellison et al.

[11] Patent Number: Plant 8,318

[45] Date of Patent: Jul. 20, 1993

[54] ASPARAGUS PLANT NAMED AUSTIN

[75] Inventors: J. Howard Ellison, Milltown; John J. Kinelski, Princeton, both of N.J.

[73] Assignee: Rutgers University, New Brunswick, N.J.

[21] Appl. No.: 793,099

[22] Filed: Nov. 15, 1991

[51] Int. Cl.[5] ..... A01H 5/00

[52] U.S. Cl. ..... Plt./95

[58] Field of Search ..... Plt./95

*Primary Examiner*—James R. Feyrer

*Attorney, Agent, or Firm*—Frank B. Robb

[57] ABSTRACT

A male asparagus plant developed from a persistent green male parent and because when crossed with a normal female plant, produces only male progeny and is thus homogametic for maleness, and is a hybrid that is superior in specific asparagus growing regions which may have long, dry growing seasons.

1 Drawing Sheet

BACKGROUND OF THE INVENTION

As an on going program of development of asparagus plants for various conditions, the instant plant is one of the products of a development process which has been extended over more than thirty years and in which the various results have been directed to specific problems arising during that period of time or before and as a result of difficulties with certain known old asparagus plants such as the "Mary Washington" and "Martha Washington" varieties.

While a good deal of the experimentation and the ultimate results have been analyzed and recorded as a result of these experiments carried on in the state of New Jersey, at the same time there are other asparagus growing regions which have other problems although some of the same as may exist in New Jersey.

SPECIFIC DETAILS OF THE INVENTION

It is noted that the invention hereof particularly deals with a male asparagus plant and as is the case in all the recorded experiments which have been conducted by us, it has been assigned the plant No. 50-2 for identification purposes in our records, and for commercial purposes we have chosen to denominate the plant as "Austin".

The plant 'Austin' was selected from among the progeny of a parent plant which is identified in our records as 'No. 50'. The parent plant 'No. 50' was, itself, a selection from a field of 'Washington' asparagus in Salem County, N.J. Plant 'No. 50' is a male and female fertile plant which was believed to be heterozygous for gender at each loci. This parent plant was self-pollinated, and produced a number of individuals having a homogametic male character and from which the plant named 'Austin' was selected. 'Austin' has been progeny tested by crossing with female asparagus plants and has been found to produce only male progeny and is thus confirmed to be homogametic for maleness. Upon determining that the instant plant was homogametic for maleness through the progeny testing indicated above, 'Austin' was selected for introduction and for potential use of this plant in breeding systems and seed production where all male progeny in the form of F1 hybrid seed are desired to be produced with certitude.

'Austin' is also homozygous for another desirable trait that we term the "persistent green" (gg) character. This term is one selected for a single recessive gene discovered in asparagus. It is a conspicuous marker gene and in the homozygous state expresses the dark green foliage color, which never turns yellow in the fall. Thus, when 'Austin' is selectively crossed with female lines which are also persistent green, the F1 seed from selected female parents produce seed which develop into plants which are all male as well as persistent green. Such F1 hybrid seed, which will produce plants of such character, is believed to represent seed of superior value due to the value of these outstanding traits as well as due to the inherent purity of seed so produced which render plants which share these traits.

The persistent green characteristic is one of the most distinguishing characteristics of 'Austin' and we have thus, in turn, chosen to use the term "persistent green" to further emphasize this characteristic in a somewhat different way.

This particular plant being an all male plant has been selected for the characteristic which it carries, producing all male asparagus progeny when crossed with female asparagus plants of several different forms.

The invention hereof in the asparagus plant, as being a male also produces all male persistent green progeny when crossed with persistent green females. Persistent green plants may be well adapted to asparagus producing regions with long, dry, growing seasons.

As will be understood, the long continuing program which has been undertaken and of which we have been a part, has been primarily directed to the ultimate production of hybrid seed and in consequence thereof the instant male asparagus plant has been found to be particularly valuable in this connection, carrying out the usual procedure in producing hybrid seed by placing the particular plant hereof in cages or in an isolated area with selected female plants, these being availed of during the flowering period and to transfer pollen from the male hereof to the females with which it is associated.

The berries resulting from this pollination contain hybrid asparagus seed. The seed is extracted, cleaned, dried, and planted to establish fields or gardens.

It has been found that this particular male plant is unique in that it is both persistent green and homogametic for maleness. It also produces all male hybrids when crossed with normal females and persistent green, all-male hybrids when crossed with persistent green females.

While the primary objective of this has been to provide for seed production, it is also notable that this particular plant of the invention has been caused to be asexually reproduced by us and found to carry the various characteristics which are thought to be important from generation to generation without modification.

The asparagus plant 'Austin' hereof was vegetatively propagated by us in the tissue culture laboratory in the Horticulture Department at Rutgers University.

As before stated the fact that seed production is usually the objective of asparagus development, it is found however that the male characteristic is persistent.

As will be understood from a consideration of the data supplied herewith, the asparagus plant hereof is a very valuable producer and the data is such as to support the allegations of same.

Figure 1:
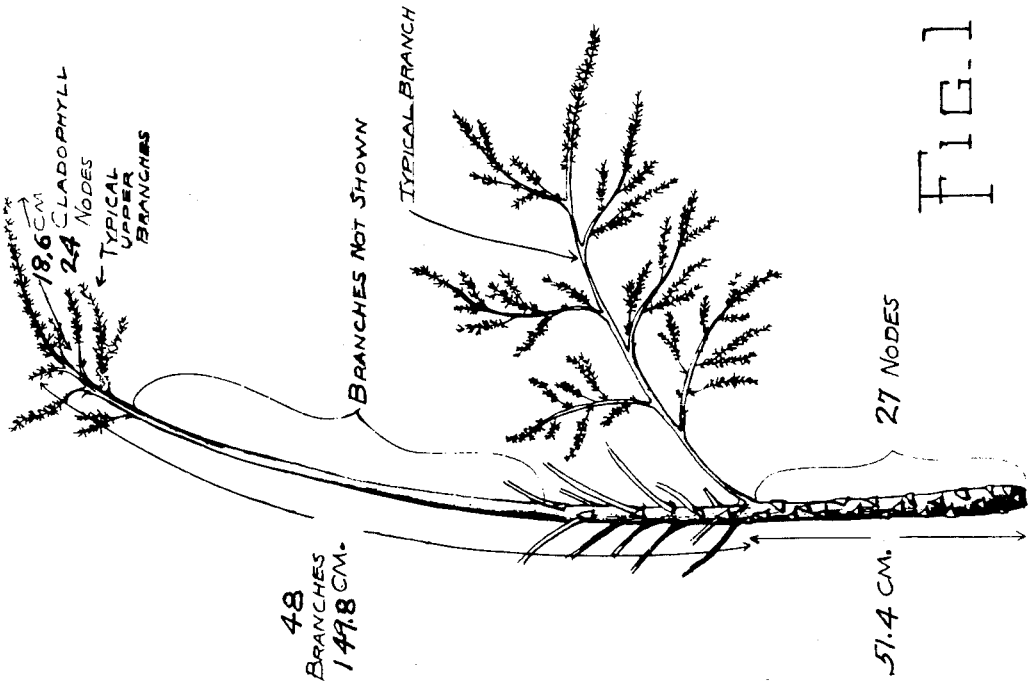

It is also notable that in the drawing, supplied herewith,

FIG. 1 discloses a typical asparagus stalk with the various dimensions thereon and including measurements which will help to distinguish this particular plant from others, in our program as well as in other asparagus growing programs.

FIG. 2 of the drawing discloses a typical asparagus plant, in order to disclose the same as it ultimately matures.

As will be further understood, any reference to color data is made as the result of comparison with the Munsell Limit Color Cascade which is a standard work for such comparisons and that is the basis therefore. It should also be understood that the color is as nearly like that of the actual plant as is possible to provide by color photography, such as is availed of here.

Stalk Data:

*Number of nodes below first branch* (1).—27.
*Number of cm from crown to first branch* (1).—63.9.
*Number of branches* (1).—49.
*Number of cm between first and last branch* (1).—123.4.
*Internode length in cm between branches* (1).—2.55.
*Number of cladophyll nodes beyond last branch* (1).—26.
*Number of cm beyond last branch* (1).—16.3.
*Internode length in cm beyond last branch* (1).—0.63.
*Largest stalk diameter in mm.*—14.
*Mean diameter of three largest stalks in mm.*—13.2.
*Number of stalks.*—9.
*Stalk vigor index* (*No.* × *mean diameter*$^2$).—1,600.
*Mature stalk color, bloom removed. Color No.* *.—21-21.
*Crown to first branch of highest headed stalk.*—57.8.

Flower data:

*Petal tip (yellow) Color No.* *.—24-9.
*Petal base (green) Color No.* *.—24-12.
*Flower length in mm.*—5.44.
*Flower width at midpoint in mm.*—2.33.
*Style length in mm.*—1.04.

Cladophyll data:

*Number per node.*—5.43.
*Length in mm.*—17.93.
*Width in mm.*—0.125.

TABLE 1

Yield of asparagus at Donald Cook Farms, Republic of South Africa.

| Variety | Yield, kg/ha 1981 | 1982 | 1983 | 1984 | 1985 | Total |
|---|---|---|---|---|---|---|
| Limbras | 328 | 823 | 908 | 1066 | 949 | 4074 |
| V15X50-9 | 524 | 818 | 906 | 1200 | 872 | 4320 |
| Jersey Jewel | 578 | 1715 | 1662 | 1810 | 1726 | 7491 |

zPlanted in 1979.

TABLE 2

Size and quality of asparagus spears - Donald Cook Farms, Republic of South Africa.z

| Variety | Spear weight grams/spear | Grade No. 1 % |
|---|---|---|
| Limbras | 10.1 | 14.0 |
| V15X50-9 | 12.6 | 47.9 |
| Jersey Jewel | 11.5 | 31.3 |

zPlanted 1979. Data from 1985 harvest.

We claim:

1. An asparagus plant as herein shown and described, characterized as to novelty, which is homogametic for maleness and has the ability when crossed with persistent green females to produce plants which are well adapted to asparagus producing regions with long, dry, growing seasons, and providing high yield therefrom.

* * * * *